US009339403B2

(12) United States Patent
Furst et al.

(10) Patent No.: US 9,339,403 B2

(45) Date of Patent: May 17, 2016

(54) MEDICAL ADHESIVE FOR MEDICAL DEVICES

(75) Inventors: Joseph G. Furst, Lyndhurst, OH (US); Ravish Sachar, Raleigh, NC (US)

(73) Assignee: ICON MEDICAL CORP., Atlanta, GA (US)

( * ) Notice: Subject to any disclaimer, the term of this patent is extended or adjusted under 35 U.S.C. 154(b) by 2280 days.

(21) Appl. No.: 11/367,850

(22) Filed: Mar. 3, 2006

(65) Prior Publication Data

US 2006/0206189 A1 Sep. 14, 2006

Related U.S. Application Data

(63) Continuation-in-part of application No. 11/271,528, filed on Nov. 12, 2005, now Pat. No. 7,455,688.

(60) Provisional application No. 60/658,401, filed on Mar. 3, 2005, provisional application No. 60/627,421, filed on Nov. 12, 2004, provisional application No. 60/658,289, filed on Mar. 3, 2005.

(51) Int. Cl.

*A61F 2/95* (2013.01)
*A61F 2/958* (2013.01)
*A61F 2/82* (2013.01)

(52) U.S. Cl.

CPC . *A61F 2/958* (2013.01); *A61F 2/95* (2013.01); *A61F 2002/821* (2013.01); *A61F 2002/9583* (2013.01)

(58) Field of Classification Search

CPC .... A61F 2002/9583; A61F 2/95; A61F 2/958
USPC ................................................ 623/1.11, 1.12
See application file for complete search history.

(56) References Cited

U.S. PATENT DOCUMENTS 5,263,349 A 11/1993 Felix et al.
5,387,450 A * 2/1995 Stewart ................ A61L 15/585 428/339

(Continued)

FOREIGN PATENT DOCUMENTS

CA 2172187 6/2001
EP 734721 2/1996

(Continued)

OTHER PUBLICATIONS

Silicon Micromachined Hollow Microneedles for Transdermal Liquid Transport, Jan J.G.E. Gardeniers, Regina Luttge, Erwin J.W. Berenschot, Meint J. De Boer, Shuki Y. Yeshurun, Meir Hefetz, Ronnyb van't Oever, and Abert van den Berg, Journal of Microelectromechanical Systems, vol. 12, No. 6, Dec. 2003.

(Continued)

*Primary Examiner* — Elizabeth Houston
*Assistant Examiner* — Michael Mendoza
(74) *Attorney, Agent, or Firm* — Fay Sharpe LLP

(57) ABSTRACT

A medical treatment device that includes a medical adhesive and a medical device. The medical adhesive is formulated to at least partially physically retain the medical device in a particular form until the medical device is at least partially deployed to a treatment area and/or to at least partially physical connect the medical device to a deployment device until the medical device is at least partially deployed to a treatment area. The medical adhesive can include at least one biological agent.

5 Claims, 2 Drawing Sheets

(56) References Cited

U.S. PATENT DOCUMENTS

| | | | | |
|---|---|---|---|---|
| 5,437,744 | A | 8/1995 | Carlen | |
| 5,556,754 | A | 9/1996 | Singer | |
| 5,578,645 | A | 11/1996 | Askanazi | |
| 5,605,696 | A | 2/1997 | Eury | |
| 5,632,840 | A | 5/1997 | Campbell | |
| 5,643,278 | A * | 7/1997 | Wijay | 623/1.11 |
| 5,649,977 | A | 7/1997 | Campbell | |
| 5,843,172 | A | 12/1998 | Yan | |
| 5,871,437 | A * | 2/1999 | Alt | 600/3 |
| 5,873,811 | A * | 2/1999 | Wang et al. | 600/3 |
| 6,066,156 | A * | 5/2000 | Yan | A61F 2/95 604/96.01 |
| 6,093,520 | A | 7/2000 | Vladimirsky | |
| 6,102,943 | A * | 8/2000 | McGuinness | 623/1.12 |
| 6,240,616 | B1 | 6/2001 | Yan | |
| 6,302,906 | B1 * | 10/2001 | Goicoechea et al. | 623/1.11 |
| 6,334,856 | B1 | 1/2002 | Allen et al. | |
| 6,365,616 | B1 | 4/2002 | Kohn | |
| 6,398,863 | B1 | 6/2002 | Okinaka et al. | |
| 6,533,949 | B1 | 3/2003 | Yeshurun | |
| 6,558,361 | B1 | 5/2003 | Yeshurun | |
| 6,709,440 | B2 * | 3/2004 | Matin et al. | 606/108 |
| 6,861,406 | B2 | 3/2005 | Mascarenhas | |
| 6,887,851 | B2 | 5/2005 | Mascarenhas | |
| 6,899,727 | B2 | 5/2005 | Armstrong | |
| 6,902,572 | B2 | 6/2005 | Beulke | |
| 6,914,049 | B2 | 7/2005 | Mascarenhas | |
| 6,942,682 | B2 | 9/2005 | Vrba et al. | |
| 6,955,661 | B1 | 10/2005 | Herweck | |
| 6,955,685 | B2 | 10/2005 | Escamilla | |
| 6,964,681 | B2 | 11/2005 | Murray, III | |
| 6,966,923 | B2 | 11/2005 | Gittings | |
| 6,979,347 | B1 | 12/2005 | Wu et al. | |
| 2001/0013166 | A1 | 8/2001 | Yan | |
| 2002/0082679 | A1 | 6/2002 | Sirhan et al. | |
| 2002/0098278 | A1 | 7/2002 | Bates | |
| 2002/0142974 | A1 | 10/2002 | Kohn | |
| 2002/0155737 | A1 | 10/2002 | Roy | |
| 2003/0100499 | A1 | 5/2003 | Epstein | |
| 2004/0024448 | A1 * | 2/2004 | Chang et al. | 623/1.42 |
| 2004/0072105 | A1 | 4/2004 | Yeshurun | |
| 2004/0098014 | A1 | 5/2004 | Flugelman | |
| 2005/0029223 | A1 | 2/2005 | Yeshurun | |
| 2005/0165358 | A1 | 7/2005 | Yeshurun | |
| 2005/0209566 | A1 | 9/2005 | Yeshurun | |
| 2006/0051404 | A1 | 3/2006 | Yeshurun | |

FOREIGN PATENT DOCUMENTS

| | | |
|---|---|---|
| EP | 714640 | 6/1996 |
| EP | 756853 | 2/1997 |
| WO | WO 00/12175 | 3/2000 |
| WO | WO 01/41678 | 6/2001 |

OTHER PUBLICATIONS

Matsuda, 2002. Device-directed therapeutic drug delivery systems. Journal of Controlled Release, vol. 78:125-131.

Regar et al., 2001. Stent development and local drug delivery. British Medical Bulletin, vol. 59:277-248/.

Metals handbook Desk Edition, 2$^{nd}$ Edition. Copyright 1998 by ASM Intl.

* cited by examiner

MEDICAL ADHESIVE FOR MEDICAL DEVICES

The present invention claims priority on U.S. Provisional Application Ser. No. 60/658,401 filed Mar. 3, 2005, entitled "MEDICAL ADHESIVE FOR MEDICAL DEVICES", which is incorporated herein.

The present invention is also a continuation-in-part of U.S. patent application Ser. No. 11/271,528 filed Nov. 12, 2005 now U.S. Pat. No. 7,455,688, entitled "OSTIOLE STENT", which in turn claims priority on U.S. Provisional Application Ser. Nos. 60/627,421 filed Nov. 12, 2004, entitled "OSTIOLE STENT", and 60/658,289 filed Mar. 3, 2005, entitled "OSTIOLE STENT", all three of which are incorporated herein by reference.

The present invention is directed to medical devices and more particularly to a device and method for physically retaining a medical device in a particular form and/or on a particular deployment device until the medical device is positioned in a desired location.

BACKGROUND OF THE INVENTION

The use of stents in blood vessels and other structures in the body has become a well established clinical procedure over the past several years. The equipment and techniques for deploying stents inside blood vessels are well established. Most stents currently available are deployed by being crimped to an angioplasty balloon. During some procedures, the stent becomes mispositioned on the angioplasty balloon or completely disengages from the balloon. When this occurs, the stent has to be retrieved and the insertion procedure has to be repeated.

Some medical devices have physical properties that make such devices potentially unstable before the device can be properly positioned during a medical procedure. One such device is a self expanding stent. These stents are typically designed to expand after being heated by the body to a certain temperature. If a medical procedure takes too long or is delayed, or the stent becomes dislodged during an insertion procedure, such stent can prematurely expand before the stent is properly positioned.

In view of the current state of art, there is a need for a device and method for physically retaining a medical device in a particular form and/or on a particular deployment device until the medical device is properly positioned in a desired location.

SUMMARY OF THE INVENTION

The present invention is directed to a device and method for physically retaining a medical device in a particular form and/or on a particular deployment device until the medical device is properly positioned at a desired location.

In one non-limiting aspect of the invention, there is provided a medical adhesive that is applied to, included in and/or is used in conjunction with one or more medical devices. The medical adhesive of the present invention is distinguished from standard adhesives that are used on prior art adhesives such as DURMABOND or prior art adhesives on band-aids, surgical tape, medical tape, STERI-STRIP, and the like in that the medical adhesive of the present invention is designed to be used with and/or in conjunction with a medical device for a limited period of time and then 1) disengage from the medical device after the medical device has been partially or fully deployed and/or 2) dissolve and/or degrade during and/or after the medical device has been partially or fully deployed. Prior art band-aids, surgical tape, medical tape, STERI-STRIP and the like include an adhesive that is designed to maintain the tape, band-aid, etc. on the patient until the tape, band-aid, etc. has performed its desired function, and thereafter, the medical device is removed from the patient. DURMABOND is an adhesive that is not used with another medical device and is designed to close small cuts in skin. The medical adhesive of the present invention is designed and formulated to be temporarily used with a medical device to facilitate in the deployment of the medical device. In one non-limiting embodiment of the invention, the medical adhesive is formulated to at least partially secure a medical device (e.g., stent, PFO (patent foramen ovale) device, other types of grafts, prosthetic device, etc.) on a device (e.g., angioplasty balloon, sheath, insertion tool, etc.) that is used to at least partially transport the medical device to a location for treatment. In still another and/or alternative non-limiting embodiment of the invention, the medical adhesive is formulated to at least partially maintain a medical device (e.g., self expanding stent, etc.) in a particular shape or form until the medical device is at least partially positioned in a treatment location. In yet another and/or alternative non-limiting embodiment of the invention, the medical adhesive is formulated to at least partially maintain and/or secure one type of medical device to another type of medical device (e.g., a sheath on a self expanding stent, etc.) until the medical device is at least partially positioned in a treatment location. In still yet another and/or alternative non-limiting embodiment of the invention, the medical adhesive can be designed and/or formulated to be used with a medical device to facilitate in the use of the medical device. In one non-limiting aspect of this embodiment of the invention, the medical adhesive is formulated to at least partially secure a medical device (e.g., stent, PFO (patent foramen ovale) device, other types of grafts, prosthetic device, etc.) to a treatment area (e.g., blood vessel wall, surface of a heart, intestinal wall, stomach wall, etc.) so as to facilitate in maintaining the medical device on a treatment area. In another and/or alternative non-limiting embodiment of the invention, the medical adhesive can be used to facilitate in maintaining a medical device (e.g., prosthetic device, PFO device, etc.) on and/or at a treatment area until the medical device is properly secured to the treatment area by sutures, stitches, screws, nails, rod, etc. As can be appreciated, the medical adhesive can be included on such sutures, stitches, screws, nails, rod, etc.; however, this is not required. In still another and/or alternative non-limiting embodiment of the invention, the medical adhesive can be use to facilitate maintaining a medical device on and/or at a treatment area until the medical device has partially or fully accomplished its objective. For instance, if a duct, blood vessel or other body passageway has a weak or damaged area or an opening that needs to be reinforced, protected and/or closed, a medical device such as, but not limited to, a graft, bandage, suture strips, patch, etc. can be applied to the area of concern and the medical adhesive can be used to at least partially secure the medical device to the area of concern. As can be appreciated, the uses of the medical adhesive set forth above are only illustrative of a few of the many uses of the medical adhesive of the present invention. As used herein, the term "body passageway" is defined to be any passageway or cavity in a living organism (e.g., bile duct, bronchiole tubes, nasal cavity, blood vessels, heart, esophagus, trachea, stomach, fallopian tube, uterus, ureter, urethra, the intestines, lymphatic vessels, nasal passageways, eustachian tube, acoustic meatus, etc.). For vascular applications, the term "body passageway" primarily refers to blood vessels and chambers in the heart.

In another and/or alternative non-limiting aspect of the invention, the medical adhesive is a biocompatible material so as to not cause unanticipated adverse effects when properly used. The medical adhesive can be biostable or biodegradable (i.e., dissolves, degrades, is absorbed, or any combination thereof in the body). The adhesive can be formulated to withstand sterilization of a medical device; however, this is not required. The medical adhesive can be formed of a variety of materials such as, but not limited to, silicone materials, cyanoacylate polymer, glutaraldehyde compositions, polypropylene-based resin and/or a hydrocolloid adhesive composition.

In still another and/or alternative non-limiting aspect of the invention, the medical adhesive can be applied by one or more techniques such as, but not limited to, spraying (e.g., atomizing spray techniques, etc.), dip coating, roll coating, sonication, brushing, plasma deposition, vapor deposition, impregnated, etc. The medical adhesive can be applied on and/or in a medical device, and/or be used to form at least a part of the medical device. One or more regions and/or surfaces of a medical device can include the medical adhesive.

In yet another and/or alternative non-limiting aspect of the invention, the medical adhesive can include one or more biological agents that facilitate in the success of the medical device and/or treated area. The term "biological agent" includes, but is not limited to, a substance, drug, or otherwise formulated and/or designed to prevent, inhibit and/or treat one or more biological problems, and/or to promote the healing in a treated area. Non-limiting examples of biological problems that can be addressed by one or more biological agents include, but are not limited to, viral, fungus and/or bacteria infection; vascular diseases and/or disorders; digestive diseases and/or disorders; reproductive diseases and/or disorders; lymphatic diseases and/or disorders; cancer; implant rejection; pain; nausea; swelling; arthritis; bone diseases and/or disorders; organ failure; immunity diseases and/or disorders; cholesterol problems; blood diseases and/or disorders; lung diseases and/or disorders; heart diseases and/or disorders; brain diseases and/or disorders; neuralgia diseases and/or disorders; kidney diseases and/or disorders; ulcers; liver diseases and/or disorders; intestinal diseases and/or disorders; gallbladder diseases and/or disorders; pancreatic diseases and/or disorders; psychological disorders; respiratory diseases and/or disorders; gland diseases and/or disorders; skin diseases and/or disorders; hearing diseases and/or disorders; oral diseases and/or disorders; nasal diseases and/or disorders; eye diseases and/or disorders; fatigue; genetic diseases and/or disorders; burns; scarring and/or scars; trauma; weight diseases and/or disorders; addiction diseases and/or disorders; hair loss; cramps; muscle spasms; tissue repair; and/or the like. Non-limiting examples of biological agents that can be used include, but are not limited to, 5-Fluorouracil and/or derivatives thereof; 5-Phenylmethimazole and/or derivatives thereof; ACE inhibitors and/or derivatives thereof; acenocoumarol and/or derivatives thereof; acyclovir and/or derivatives thereof; actilyse and/or derivatives thereof; adrenocorticotropic hormone and/or derivatives thereof; adriamycin and/or derivatives thereof; agents that modulate intracellular $Ca_{2+}$ transport such as L-type (e.g., diltiazem, nifedipine, verapamil, etc.) or T-type $Ca_{2+}$ channel blockers (e.g., amiloride, etc.); alpha-adrenergic blocking agents and/or derivatives thereof; alteplase and/or derivatives thereof; amino glycosides and/or derivatives thereof (e.g., gentamycin, tobramycin, etc.); angiopeptin and/or derivatives thereof; angiostatic steroid and/or derivatives thereof; angiotensin II receptor antagonists and/or derivatives thereof; anistreplase and/or derivatives thereof; antagonists of vascular epithelial growth factor and/or derivatives thereof; anti-biotics; anti-coagulant compounds and/or derivatives thereof; anti-fibrosis compounds and/or derivatives thereof; anti-fungal compounds and/or derivatives thereof; anti-inflammatory compounds and/or derivatives thereof; Anti-Invasive Factor and/or derivatives thereof; anti-metabolite compounds and/or derivatives thereof (e.g., staurosporin, trichothecenes, and modified diphtheria and ricin toxins, *Pseudomonas* exotoxin, etc.); anti-matrix compounds and/or derivatives thereof (e.g., colchicine, tamoxifen, etc.); anti-microbial agents and/or derivatives thereof; anti-migratory agents and/or derivatives thereof (e.g., caffeic acid derivatives, nilvadipine, etc.); anti-mitotic compounds and/or derivatives thereof; anti-neoplastic compounds and/or derivatives thereof; anti-oxidants and/or derivatives thereof; anti-platelet compounds and/or derivatives thereof; anti-proliferative and/or derivatives thereof; anti-thrombogenic agents and/or derivatives thereof; argatroban and/or derivatives thereof; ap-1 inhibitors and/or derivatives thereof (e.g., for tyrosine kinase, protein kinase C, myosin light chain kinase, $Ca_{2+}$/calmodulin kinase II, casein kinase II, etc.); aspirin and/or derivatives thereof; azathioprine and/or derivatives thereof; β-Estradiol and/or derivatives thereof; β-1-anticollagenase and/or derivatives thereof; calcium channel blockers and/or derivatives thereof; calmodulin antagonists and/or derivatives thereof (e.g., $H_7$, etc.); CAPTOPRIL and/or derivatives thereof; cartilage-derived inhibitor and/or derivatives thereof; ChIMP-3 and/or derivatives thereof; cephalosporin and/or derivatives thereof (e.g., cefadroxil, cefazolin, cefaclor, etc.); chloroquine and/or derivatives thereof; chemotherapeutic compounds and/or derivatives thereof (e.g., 5-fluorouracil, vincristine, vinblastine, cisplatin, doxyrubicin, adriamycin, tamocifen, etc.); chymostatin and/or derivatives thereof; CILAZAPRIL and/or derivatives thereof; clopidigrel and/or derivatives thereof, clotrimazole and/or derivatives thereof; colchicine and/or derivatives thereof; cortisone and/or derivatives thereof; coumadin and/or derivatives thereof; curacin-A and/or derivatives thereof; cyclosporine and/or derivatives thereof; cytochalasin and/or derivatives thereof (e.g., cytochalasin A, cytochalasin B, cytochalasin C, cytochalasin D, cytochalasin E, cytochalasin F, cytochalasin G, cytochalasin H, cytochalasin J, cytochalasin K, cytochalasin L, cytochalasin M, cytochalasin N, cytochalasin O, cytochalasin P, cytochalasin Q, cytochalasin R, cytochalasin S, chaetoglobosin A, chaetoglobosin B, chaetoglobosin C, chaetoglobosin D, chaetoglobosin E, chaetoglobosin F, chaetoglobosin G, chaetoglobosin J, chaetoglobosin K, deoxaphomin, proxiphomin, protophomin, zygosporin D, zygosporin E, zygosporin F, zygosporin G, aspochalasin B, aspochalasin C, aspochalasin D, etc.); cytokines and/or derivatives thereof; desirudin and/or derivatives thereof; dexamethazone and/or derivatives thereof; dipyridamole and/or derivatives thereof; eminase and/or derivatives thereof; endothelin and/or derivatives thereof; endothelial growth factor and/or derivatives thereof; epidermal growth factor and/or derivatives thereof; epothilone and/or derivatives thereof; estramustine and/or derivatives thereof; estrogen and/or derivatives thereof; fenoprofen and/or derivatives thereof; fluorouracil and/or derivatives thereof; flucytosine and/or derivatives thereof; forskolin and/or derivatives thereof; ganciclovir and/or derivatives thereof; glucocorticoids and/or derivatives thereof (e.g., dexamethasone, betamethasone, etc.); glycoprotein IIb/IIIa platelet membrane receptor antibody and/or derivatives thereof; GM-CSF and/or derivatives thereof; griseofulvin and/or derivatives thereof; growth factors and/or derivatives thereof (e.g., VEGF; TGF; IGF; PDGF; FGF, etc.); growth hormone and/or derivatives thereof; heparin and/or derivatives thereof; hirudin and/or derivatives thereof; hyaluronate and/or derivatives thereof; hydrocortisone and/or derivatives thereof; ibuprofen and/or derivatives thereof; immunosuppressive agents and/or derivatives thereof (e.g., adrenocorticosteroids, cyclosporine, etc.); indomethacin and/or derivatives thereof; inhibitors of the sodium/calcium antiporter and/or derivatives thereof (e.g., amiloride, etc.); inhibitors of the $IP_3$ receptor and/or derivatives thereof; inhibitors of the sodium/hydrogen antiporter and/or derivatives thereof (e.g., amiloride and derivatives thereof, etc.); insulin and/or derivatives thereof; Interferon alpha 2 Macroglobulin and/or derivatives thereof; ketoconazole and/or derivatives thereof; Lepirudin and/or derivatives thereof; LISINOPRIL and/or derivatives thereof; LOVASTATIN and/or derivatives thereof; marevan and/or derivatives thereof; mefloquine and/or derivatives thereof; metalloproteinase inhibitors and/or derivatives thereof; methotrexate and/or derivatives thereof; metronidazole and/or derivatives thereof; miconazole and/or derivatives thereof; monoclonal antibodies and/or derivatives thereof; mutamycin and/or derivatives thereof; naproxen and/or derivatives thereof; nitric oxide and/or derivatives thereof; nitroprusside and/or derivatives thereof; nucleic acid analogues and/or derivatives thereof (e.g., peptide nucleic acids, etc.); nystatin and/or derivatives thereof; oligonucleotides and/or derivatives thereof; paclitaxel and/or derivatives thereof; penicillin and/or derivatives thereof; pentamidine isethionate and/or derivatives thereof; phenindione and/or derivatives thereof; phenylbutazone and/or derivatives thereof; phosphodiesterase inhibitors and/or derivatives thereof; Plasminogen Activator Inhibitor-1 and/or derivatives thereof; Plasminogen Activator Inhibitor-2 and/or derivatives thereof; Platelet Factor 4 and/or derivatives thereof; platelet derived growth factor and/or derivatives thereof; plavix and/or derivatives thereof; POSTMI 75 and/or derivatives thereof; prednisone and/or derivatives thereof; prednisolone and/or derivatives thereof; probucol and/or derivatives thereof; progesterone and/or derivatives thereof; prostacyclin and/or derivatives thereof; prostaglandin inhibitors and/or derivatives thereof; protamine and/or derivatives thereof; protease and/or derivatives thereof; protein kinase inhibitors and/or derivatives thereof (e.g., staurosporin, etc.); quinine and/or derivatives thereof; radioactive agents and/or derivatives thereof (e.g., Cu-64, Ca-67, Cs-131, Ga-68, Zr-89, Ku-97, Tc-99m, Rh-105, Pd-103, Pd-109, In-111, I-123, I-125, I-131, Re-186, Re-188, Au-198, Au-199, Pb-203, At-211, Pb-212, Bi-212, $H_3P^{32}O_4$, etc.); rapamycin and/or derivatives thereof; receptor antagonists for histamine and/or derivatives thereof; refludan and/or derivatives thereof; retinoic acids and/or derivatives thereof; revasc and/or derivatives thereof; rifamycin and/or derivatives thereof; sense or anti-sense oligonucleotides and/or derivatives thereof (e.g., DNA, RNA, plasmid DNA, plasmid RNA, etc.); seramin and/or derivatives thereof; steroids; seramin and/or derivatives thereof; serotonin and/or derivatives thereof; serotonin blockers and/or derivatives thereof; streptokinase and/or derivatives thereof; sulfasalazine and/or derivatives thereof; sulfonamides and/or derivatives thereof (e.g., sulfamethoxazole, etc.); sulphated chitin derivatives; Sulphated Polysaccharide Peptidoglycan Complex and/or derivatives thereof; $T_{H1}$ and/or derivatives thereof (e.g., Interleukins-2, -12, and -15, gamma interferon, etc.); thioprotese inhibitors and/or derivatives thereof; taxol and/or derivatives thereof (e.g., taxotere, baccatin, 10-deacetyltaxol, 7-xylosyl-10-deacetyltaxol, cephalomannine, 10-deacetyl-7-epitaxol, 7 epitaxol, 10-deacetylbaccatin III, 10-deacetylcephaolmannine, etc.); ticlid and/or derivatives thereof; ticlopidine and/or derivatives thereof; tick anti-coagulant peptide and/or derivatives thereof; thioprotese inhibitors and/or derivatives thereof; thyroid hormone and/or derivatives thereof; Tissue Inhibitor of Metalloproteinase-1 and/or derivatives thereof; Tissue Inhibitor of Metalloproteinase-2 and/or derivatives thereof; tissue plasma activators; TNF and/or derivatives thereof, tocopherol and/or derivatives thereof; toxins and/or derivatives thereof; tranilast and/or derivatives thereof; transforming growth factors alpha and beta and/or derivatives thereof; trapidil and/or derivatives thereof; triazolopyrimidine and/or derivatives thereof; vapiprost and/or derivatives thereof; vinblastine and/or derivatives thereof; vincristine and/or derivatives thereof; zidovudine and/or derivatives thereof. As can be appreciated, the biological agent can include one or more derivatives of the above listed compounds and/or other compounds. In one non-limiting embodiment, the biological agent includes, but is not limited to, trapidil, trapidil derivatives, taxol, taxol derivatives, cytochalasin, cytochalasin derivatives, paclitaxel, paclitaxel derivatives, rapamycin, rapamycin derivatives, 5-Phenylmethimazole, 5-Phenylmethimazole derivatives, GM-CSF, GM-CSF derivatives, or combinations thereof. The type and/or amount of biological agent included on, in and/or in conjunction with the medical adhesive is generally selected for the treatment of one or more medical treatments. Typically the amount of biological agent included on, in and/or used in conjunction with the medical adhesive is about 0.01-100 ug per $mm^2$; however, other amounts can be used. When two or more biological agents are used, the amount of two of more biological agents on, in and/or used in conjunction with the medical adhesive can be the same or different.

In a further and/or alternative non-limiting aspect of the present invention, when one or more biological agents are used in, on and/or with the medical adhesive, the one or more biological agents can be released in a controlled manner so the area in question to be treated is provided with the desired dosage of biological agent over a sustained period of time. As can be appreciated, controlled release of one or more biological agents is not always required and/or desirable. As such, one or more of the biological agents can be uncontrollably released during and/or after insertion of a medical device in the treatment area. It can also be appreciated that one or more biological agents can be controllably released and one or more biological agents can be uncontrollably released during and/or after insertion of a medical device in the treatment area. It can also be appreciated that one or more biological agents can be controllably released and one or more biological agents can be uncontrollably released during and/or after insertion of a medical device in the treatment area. The rate of release of the one or more biological agents can be the same or different. One non-limiting arrangement that can be used to control the release of one or more biological agent from the medical adhesive include a) at least partially incorporating and/or at least partially encapsulating one or more biological agents in the medical adhesive. As can be appreciated, other or additional arrangements can be used to control the release of one or more biological agent from the medical adhesive. The concentration of one or more biological agents used on, in and/or in conjunction with the medical adhesive can be used to control the release time, the release rate and/or the dosage amount of one or more biological agents; however, other or additional combinations can be used. As can also be appreciated, one or more biological agents can be deposited on the top surface of the medical adhesive to provide an initial uncontrolled burst effect of the one or more biological agents prior to the control release of the one or more biological agents from the medical adhesive and/or a medical device The one or more biological agents can be coated on the medical adhesive by a variety of mechanisms such as, but not limited to, spraying (e.g., atomizing spray techniques, etc.), dip coating, roll coating, sonication, brushing, plasma deposition, and/or depositing by vapor deposition.

In still a further and/or alternative non-limiting aspect of the present invention, when one or more biological agents are used with the medical adhesive, the medical adhesive can be used to control the release of one or more biological agents located on a medical device by forming a penetrable or non-penetrable barrier to such biological agents. When the medical adhesive forms a penetrable barrier, the medical adhesive can be formulated to have a structure that controls the rate at which one or more biological agents can penetrate the barrier formed by the medical adhesive; however, this is not required. When the medical adhesive forms a non-penetrable barrier, the medical adhesive can be formulated to be a degradable adhesive that degrades over a period of time to eventually remove the barrier formed by the medical adhesive; however, this is not required. As can be appreciated, the medical adhesive can be formulated to be a penetrable barrier for some types of biological agents and a non-penetrable barrier for other types of biological agents.

In yet a further and/or alternative non-limiting aspect of the present invention, the medical adhesive can include a material that functions as a marker. The marker material is typically designed to be visible to electromagnetic waves (e.g., x-rays, micro-waves, visible light, inferred waves, ultraviolet waves, etc.); sound waves (e.g, ultrasound waves, etc.); and/or magnetic waves (e.g., MRI, etc.). In one non-limiting embodiment of the invention, the marker material is visible to x-rays (i.e., radiopaque). The marker material can be used to facilitate in the placement of a medical device in or on a desired location. The marker material can also or alternatively be used to provide information as to 1) the location of the medical adhesive on and/or in a medical device, 2) whether the medical adhesive has been properly applied to a medical device, and/or 3) the current state of engagement or disengagement of the medical adhesive on/from the medical device, etc. The marker material can include metal material and/or a polymer material; however, other or additional material can be used. When the marker material includes a metal material, the metal material is typically in the form of one or more metal powders and/or metal compounds. Non-limiting examples of metal material that can be used in the marker material includes, but is not limited to, aluminum, barium, bismuth, cobalt, copper, chromium, gold, iron, stainless steel, titanium, vanadium, nickel, zirconium, niobium, lead, molybdenum, platinum, yttrium, calcium, rare earth metals, rhenium, zinc, silver, depleted radioactive elements, tantalum and/or tungsten; and/or compounds thereof.

In still yet a further and/or alternative non-limiting aspect of the invention, the medical adhesive is particularly useful for use in conjunction with a medical device such as, but not limited to, a graft designed for introduction into or about a tubular body passageway and/or organ in a body. One non-limiting graft that can be used in conjunction with the medical adhesive of the present invention is a stent or PFO device. As can be appreciated, the medical adhesive can be used on other types of medical devices (e.g., prosthetic implant, suture, bandage, suture strip, patch, guide wire, balloon, sheath, vascular graft or other types of grafts, PFO device, nail, screw, rod, stitch material, etc.). One type of stent that can be used in conjunction with the medical adhesive is a stent in a blood vessel; however, the stent can be used in other regions of the body such as, but not limited to, the esophagus, trachea, colon, biliary tract, urinary tract or used as a replacement for native, synthetic, implanted or engineered organs or vessels. The stent typically includes an expandable body section. To treat a stenosis of a blood vessel, the stent is placed within the blood vessel at the diseased location and the body of the stent is radially expanded. The expansion of the vascular body member can be accomplished in a variety of manners. Typically, the stent is expanded to its second cross-sectional area by a radially, outwardly extending force applied at least partially from the interior region of the body member (e.g., the use of an angioplasty balloon, etc.). Alternatively, or additionally, the body member can include heat sensitive materials (e.g., shape memory materials, etc.) that expand upon exposure to heat. Other types of expansion can also or alternatively be used. The expandable body section of the stent can include geometric patterns and/or structural configurations that facilitate the radial expansion of the expandable body section. The expandable body section of the stent typically has sufficient radial strength to retain its expanded cross-sectional area after expansion; however, this is not required. The second cross-sectional area of the stent can be fixed or variable. When the second cross-sectional area is variable, the second cross-sectional area is typically dependent upon the amount of radially outward force applied to the stent; however, this is not required. The stent can be designed such that the body section expands while retaining the original length of the body section; however, this is not required. The body section can have a first cross-sectional shape that is generally circular so as to form a substantially tubular body section; however, the body section can have other cross-sectional shapes. When the stent includes two of more body section, the two of more body sections can be connected together by at least one connector member. The stent can be made of a uniform material, or one or more regions of the stent can be formed of different materials. Some non-limiting materials include, but are not limited to, calcium, chromium, cobalt, copper, gold, iron, lead, magnesium, molybdenum, nickel, niobium, platinum, rare earth metals, rhenium, silver, tantalum, titanium, tungsten, yttrium, zinc, zirconium, and/or alloys thereof, carbon or carbon fiber; cellulose acetate, cellulose nitrate, silicone, polyethylene terephthalate, polyurethane, polyamide, polyester, polyorthoester, polyanhydride, polyether sulfone, polycarbonate, polypropylene, high molecular weight polyethylene, polytetrafluoroethylene, polylactic acid, polyglycolic acid or copolymers thereof, a polyanhydride, polycaprolactone, polyhydroxy-butyrate valerate or another biodegradable polymer, or mixtures or copolymers of these, a protein, an extracellular matrix component, collagen, fibrin, polyethylene tetraphthlate (Dacron), polytetrafluoroethylene (e.g., Gortex, Impraflex, etc.), and/or polyurethane and/or other materials. The expandable body section can be fabricated from material that has no or substantially no shape memory characteristics (e.g., stainless steel, cobalt, chromium, magnesium, rhenium, zinc, titanium, tantalum, zirconium, etc.) or can be fabricated from a material having shape-memory characteristics (e.g., nickel-titanium alloy (nitinol)) or another metallic or non-metallic material which possesses the characteristic of shape memory. Typically when one or more shape-memory materials are used, the shape memory material composition is selected such that the shape memory material remains in an unexpanded configuration at a cold temperature (e.g., below body temperature); however, this is not required. When the shape memory material is heated (e.g., to body temperature) the expandable body section can be designed to expand to at least partially seat and/or secure the stent in the blood vessel; however, this is not required. The sections of the stent can have a uniform architectural configuration, or can have differing architectural configurations. Each of the sections of the stent can be formed of a single part or formed of multiple parts which have been attached. When a section is formed of multiple parts, typically the section is formed into one continuous piece; however, this is not required. The stent can be made of and/or include a material that is visible under electromagnetic waves, sound waves and/or magnetic waves; however, this is not required. The material to increase visibility, when used, includes, but is not limited to, metals and/or polymers. These materials can be the same as or similar to the materials that can be used to form the marker material as set forth above; however, this is not required. In one non-limiting design, the material to increase visibility, when used, can be at least partially located on at least one end of at least one stent so as to facilitate in identifying the location of the ends of the stent during the placement of the stent. The one or more markers can be formed in and/or attached to the stent and/or placed in a location on the stent so as to mark one or more particular locations on the stent such as, but not limited to, the front end, the back end, etc.; however, this is not required. The one or more markers, when used, can also or alternatively be placed on and/or in the stent at certain spaced distances so as to function as distance measuring markers. The stent can be treated with gamma, beta and/or e-beam radiation, and/or otherwise sterilized; however, this is not required. The stent can include rounded, smooth and/or blunt surfaces to minimize and/or prevent damage to a body passageway as the stent is inserted into a body passageway and/or expanded in a body passageway; however, this is not required. The stent can be composed of a biostable and/or biodegradable material. The stent can be covered with and/or include matrices of a porous and/or non-porous material; however, this is not required. The non-porous material, when used, can be formulated to allow molecular diffusion; however, this is not required. The stent can further include 1) one or more biological agents coated on the outer surface of the porous and/or non-porous material described above, 2) one or more biological agents at least partially encapsulated within the porous and/or non-porous material, and/or 3) one or more biological agents can be form a part of and/or be included within the matrices of the stent; however, this is not required. The stent can include a structure, composition and/or coating that controls the rate of release of the one or more biological agents from the stent; however, this is not required. As such, the stent can be designed such that 1) all the biological agent on the stent is controllably released, 2) some of the biological agent on the stent is controllably released and some of the biological agent on the stent is non-controllably released, or 3) none of the biological agent on the stent is controllably released. The stent can also be designed such that the rate of release of the one or more biological agents, when used, from the stent is the same or different. When the medical adhesive is inserted on the vascular graft, the medical adhesive can include one or more polymers and/or be coated on one or more polymers. The one or more polymers can be used to 1) control the time of adhesion provided by said medical adhesive, 2) control the rate of degradation of the medical adhesive, and/or 3) control the rate of biological agent release from the medical device and/or medical adhesive; however, this is not required. As can be appreciated, the one or more polymers, when used in the medical adhesive, can have other or additional functions.

In another and/or alternative non-limiting aspect of the present invention, the medical device or one or more regions of the medical device can be constructed by use of one or more microelectromechanical manufacturing techniques (MEMS (e.g., micro-machining, laser micro-machining, laser micro-machining, micro-molding, etc.); however, other or additional manufacturing techniques can be used. The medical device can include one or more surface structures (e.g., pore, channel, pit, rib, slot, notch, bump, teeth, needle, well, hole, groove, etc.). These structures can be at least partially formed by MEMS (e.g., micro-machining, etc.) technology and/or other types of technology. The medical device can include one or more micro-structures (e.g., micro-needle, micro-pore, micro-cylinder, micro-cone, micro-pyramid, micro-tube, micro-parallelopiped, micro-prism, micro-hemisphere, teeth, rib, ridge, ratchet, hinge, zipper, zip-tie like structure, etc.) on the surface of the medical device. As defined herein, a micro-structure is a structure that has at least one dimension (e.g., average width, average diameter, average height, average length, average depth, etc.) that is no more than about 2 mm, and typically no more than about 1 mm. As can be appreciated, the medical device, when including one or more surface structures, a) all the surface structures can be micro-structures, b) all the surface structures can be non-micro-structures, or c) a portion of the surface structures can be micro-structures and a portion can be non-micro-structures. Non-limiting examples of structures that can be formed on the medical devices such as stents are illustrated in United States Patent Publication Nos. 2004/0093076 and 2004/0093077, which are incorporated herein by reference. Typically, the micro-structures, when formed, extend from or into the outer surface no more than about 400 microns, and more typically less than about 300 microns, and more typically about 15-250 microns; however, other sizes can be used. The micro-structures can be clustered together or disbursed throughout the surface of the medical device. Similar shaped and/or sized micro-structures and/or surface structures can be used, or different shaped and/or sized micro-structures can be used. When one or more surface structures and/or micro-structures are designed to extend from the surface of the medical device, the one or more surface structures and/or micro-structures can be formed in the extended position and/or be designed so as to extend from the medical device during and/or after deployment of the medical device in a treatment area. The micro-structures and/or surface structures can be designed to contain and/or be fluidly connected to a passageway, cavity, etc.; however, this is not required. The one or more surface structures and/or micro-structures can be used to engage and/or penetrate surrounding tissue or organs once the medical device has be position on and/or in a patient; however, this is not required. The one or more surface structures and/or micro-structures can be used to facilitate in forming maintaining a shape of a medical device (i.e., see devices in United States Patent Publication Nos. 2004/0093076 and 2004/0093077). The one or more surface structures and/or micro-structures can be at least partially formed by MEMS (e.g., micro-machining, laser micro-machining, micro-molding, etc.) technology; however, this is not required. In one non-limiting embodiment, the one or more surface structures and/or micro-structures can be at least partially formed of a biological agent and/or be formed of a polymer. One or more of the surface structures and/or micro-structures can include one or more internal passageways that can include one or more materials (e.g., biological agent, polymer, etc.); however, this is not required. The one or more surface structures and/or micro-structures can be formed by a variety of processes (e.g., machining, chemical modifications, chemical reactions, MEMS (e.g., micro-machining, etc.), etching, laser cutting, etc.). The one or more coatings and/or one or more surface structures and/or micro-structures of the medical device can be used for a variety of purposes such as, but not limited to, 1) increasing the bonding and/or adhesion of one or more biological agents, medical adhesive, marker materials and/or polymers to the medical device, 2) changing the appearance or surface characteristics of the medical device, and/or 3) controlling the release rate of one or more biological agents. The one or more micro-structures and/or surface structures can be biostable, biodegradable, etc. One or more regions of the medical device that are at least partially formed by microelectromechanical manufacturing techniques can be biostable, biodegradable, etc. The medical device or one or more regions of the medical device can be at least partially covered and/or filled with a protective material so to at least partially protect one or more regions of the medical device, and/or one or more micro-structures and/or surface structures on the medical device from damage. One or more regions of the medical device, and/or one or more micro-structures and/or surface structures on the medical device can be damaged when the medical device is 1) packaged and/or stored, 2) unpackaged, 3) connected to and/or other secured and/or placed on another medical device, 4) inserted into a treatment area, 5) handled by a user, and/or 6) form a barrier between one or more micro-structures and/or surface structures and fluids in the body passageway. As can be appreciated, the medical device can be damaged in other or additional ways. The protective material can be used to protect the medical device and one or more micro-structures and/or surface structures from such damage. The protective material can include one or more polymers previously identified above. The protective material can be 1) biostable and/or biodegradable and/or 2) porous and/or non-porous. In one non-limiting design, the polymer is at least partially biodegradable so as to at least partially exposed one or more micro-structure and/or surface structure to the environment after the medical device has been at least partially inserted into a treatment area. In another and/or additional non-limiting design, the protective material includes, but is not limited to, sugar (e.g., glucose, fructose, sucrose, etc.), carbohydrate compound, salt (e.g., NaCl, etc.), parylene, PLGA, POE, PGA, PLLA, PAA, PEG, chitosan and/or derivatives of one or more of these materials; however, other and/or additional materials can be used. In still another and/or additional non-limiting design, the thickness of the protective material is generally less than about 300 microns, and typically less than about 150 microns; however, other thicknesses can be used. The protective material can be coated by one or more mechanisms previously described herein.

In still another and/or alternative aspect of the present invention, the medical device in the form of a stent can be deployed in its final destination by balloon expansion or, in the case of a shape memory material, by removal of a physical hindrance allowing the stent to assume its baseline shape. When the stent is at least partially formed of a spring-like, shape memory, or similar material so as to be at least partially self-expanding, the stent is typically secured to a delivery catheter in an unexpanded state or positioned in a delivery sheath and then advanced through a guiding catheter or protective sheath to a desired location. As can be appreciated, other mechanisms can be used to advance the stent to a desired site in a tubular organ. There are a number of known delivery systems for delivery of a self-expanding stent. A few such delivery systems that can be used to delivery the stent of the present invention to a desired site in a tubular organ are disclosed in U.S. Pat. Nos. 4,886,062, 4,913,141, 5,019,085, 5,147,370, 5,372,600, 5,507,768, 5,549,635, 5,607,467, 5,632,760, 5,643,278, and 5,669,932, each of which is incorporated herein by reference. Once the stent is positioned in a desired location, the stent is typically released from the delivery catheter, sheath or the like. The medical adhesive of the present invention can be used facilitate in securing or retaining the stent on the balloon, delivery catheter, etc.; however, this is not required. The physical hindrance can be solely the medical adhesive or include the medical adhesive in combination with another physical hindrance (e.g., sheath, magnet, tape, wire, string, etc.). When the medical adhesive is the physical hindrance, the medical adhesive can be applied to one or more regions of the stent to prevent or inhibit the expansion of the stent. Alternatively or additionally, the medical adhesive can be used to connect one or more regions of the stent to a delivery device (e.g., angioplasty balloon, sheath, etc.) to facilitate in maintaining the stent in an unexpanded state. When the medical adhesive and another physical hindrance are used, the medical adhesive can be applied to one or more regions of the stent to prevent or inhibit the expansion of the stent and/or the medical adhesive can be applied to one or more regions of the stent and/or other physical hindrance to inhibit or prevent the other physical hindrance from prematurely disengaging from the stent. As can be appreciated, the medical adhesive can have other or different uses when used.

In still another and/or alternative non-limiting aspect of the invention, the medical adhesive and/or medical device can be adapted to release one or more biological agents. The release of the one or more biological agents can be a random and/or controlled release. The release can be via molecular diffusion through a non-porous layer, a porous layer and/or by another arrangement; however, this is not required. The one or more biological agents, when used, in the medical adhesive and/or on the medical device can be 1) coated on one or more surfaces of the medical device, impregnated in one or regions, pours and/or cavities of the medical device, and/or 2) form a portion or be included in a portion of the structure of the medical device. When the medical adhesive includes one or more biological agents and/or one or more biological agents are coated on the medical device, medical adhesive that includes one or more biological agents can 1) be directly coated on one or more surfaces of the medical device, 2) be mixed with one or more coating polymers or other coating materials and then at least partially coated on one or more surfaces of the medical device, 3) be at least partially coated on the surface of another coating material that has been at least partially coated on the medical device, and/or 4) be at least partially encapsulated between a) a surface or region of the medical device and one or more other coating materials and/or b) two or more other coating materials. As can be appreciated, many other coating arrangements can be additionally or alternatively used. The medical adhesive can be at least partially applied over one or more regions, pours and/or cavities of the medical device to at least partially control the release of one or more biological agent in the one or more regions, pours and/or cavities of the medical device; however, this is not required. When one or more coating materials (e.g., polymer materials, etc.) are used in conjunction with the medical adhesive, the one or more coating material can be used to 1) control the release rate of one or more biological agents from the medical device and/or medical adhesive, 2) control the time of adhesion provided by said medical adhesive, and/or 3) control the rate of degradation of the medical adhesive and/or medical device; however, this is not required. As can be appreciated, the coating material can have other or additional functions. The one or more polymers that can be used can be biodegradable, bioresorbable, or bioerodable; polymers that are considered to be biostable; and/or polymers that can be made to be biodegradable and/or bioresorbable with modification. Non-limiting examples of polymers that are considered to be biodegradable, bioresorbable, or bioerodable include, but are not limited to, aliphatic polyesters; poly(glycolic acid) and/or copolymers thereof (e.g., poly(glycolide trimethylene carbonate); poly(caprolactone glycolide)); poly(lactic acid) and/or isomers thereof (e.g., poly-L(lactic acid) and/or poly-D Lactic acid) and/or copolymers thereof (e.g. DL-PLA), with and without additives (e.g. calcium phosphate glass), and/or other copolymers (e.g. poly (caprolactone lactide), poly(lactide glycolide), poly(lactic acid ethylene glycol)); poly(ethylene glycol); poly(ethylene glycol) diacrylate; poly(lactide); polyalkylene succinate; polybutylene diglycolate; polyhydroxybutyrate (PHB); polyhydroxyvalerate (PHV); polyhydroxybutyrate/polyhydroxyvalerate copolymer (PHB/PHV); poly(hydroxybutyrate-co-valerate); polyhydroxyalkaoates (PHA); polycaprolactone; poly(caprolactone-polyethylene glycol) copolymer; poly (valerolactone); polyanhydrides; poly(orthoesters) and/or blends with polyanhydrides; poly(anhydride-co-imide); polycarbonates (aliphatic); poly(hydroxyl-esters); polydioxanone; polyanhydrides; polyanhydride esters; polycyanoacrylates; poly(alkyl 2-cyanoacrylates); poly(amino acids); poly(phosphazenes); poly(propylene fumarate); poly (propylene fumarate-co-ethylene glycol); poly(fumarate anhydrides); fibrinogen; fibrin; gelatin; cellulose and/or cellulose derivatives and/or cellulosic polymers (e.g., cellulose acetate, cellulose acetate butyrate, cellulose butyrate, cellulose ethers, cellulose nitrate, cellulose propionate, cellophane); chitosan and/or chitosan derivatives (e.g., chitosan NOCC, chitosan NOOC-G); alginate; polysaccharides; starch; amylase; collagen; polycarboxylic acids; poly(ethyl ester-co-carboxylate carbonate) (and/or other tyrosine derived polycarbonates); poly(iminocarbonate); poly(BPA-iminocarbonate); poly(trimethylene carbonate); poly(iminocarbonate-amide) copolymers and/or other pseudo-poly (amino acids); poly(ethylene glycol); poly(ethylene oxide); poly(ethylene oxide)/poly(butylene terephthalate) copolymer; poly(epsilon-caprolactone-dimethyltrimethylene carbonate); poly(ester amide); poly(amino acids) and conventional synthetic polymers thereof, poly(alkylene oxalates); poly(alkylcarbonate); poly(adipic anhydride); nylon copolyamides; NO-carboxymethyl chitosan NOCC); carboxymethyl cellulose; copoly(ether-esters) (e.g., PEO/PLA dextrans); polyketals; biodegradable polyethers; biodegradable polyesters; polydihydropyrans; polydepsipeptides; polyarylates (L-tyrosine-derived) and/or free acid polyarylates; polyamides (e.g., Nylon 66, polycaprolactam); poly(propylene ftimarate-co-ethylene glycol) (e.g., fumarate anhydrides); hyaluronates; poly-p-dioxanone; polypeptides and proteins; polyphosphoester; polyphosphoester urethane; polysaccharides; pseudo-poly(amino acids); starch; terpolymer; (copolymers of glycolide, lactide, or dimethyltrimethylene carbonate); rayon; rayon triacetate; latex; and/pr copolymers, blends, and/or composites of above. Non-limiting examples of polymers that considered to be biostable include, but are not limited to, parylene; parylene c; parylene f; parylene n; parylene derivatives; maleic anyhydride polymers; phosphorylcholine; poly n-butyl methacrylate (PBMA); polyethylene-co-vinyl acetate (PEVA); PBMA/PEVA blend or copolymer; polytetrafluoroethene (Teflon®) and derivatives; poly-paraphenylene terephthalamide (Kevlar®); poly(ether ether ketone) (PEEK); poly(styrene-b-isobutylene-b-styrene) (Translute™); tetramethyldisiloxane (side chain or copolymer); polyimides polysulfides; poly(ethylene terephthalate); poly(methyl methacrylate); poly(ethylene-co-methyl methacrylate); styrene-ethylene/butylene-styrene block copolymers; ABS; SAN; acrylic polymers and/or copolymers (e.g., n-butyl-acrylate, n-butyl methacrylate, 2-ethylhexyl acrylate, lauryl-acrylate, 2-hydroxy-propyl acrylate, polyhydroxyethyl, methacrylate/methylmethacrylate copolymers); glycosaminoglycans; alkyd resins; elastin; polyether sulfones; epoxy resin; poly(oxymethylene); polyolefins; polymers of silicone; polymers of methane; polyisobutylene; ethylene-alphaolefin copolymers; polyethylene; polyacrylonitrile; fluorosilicones; poly(propylene oxide); polyvinyl aromatics (e.g. polystyrene); poly(vinyl ethers) (e.g. polyvinyl methyl ether); poly(vinyl ketones); poly(vinylidene halides) (e.g. polyvinylidene fluoride, polyvinylidene chloride); poly(vinylpyrolidone); poly(vinylpyrolidone)/vinyl acetate copolymer; polyvinylpridine prolastin or silk-elastin polymers (SELP); silicone; silicone rubber; polyurethanes (polycarbonate polyurethanes, silicone urethane polymer) (e.g., chronoflex varieties, bionate varieties); vinyl halide polymers and/or copolymers (e.g. polyvinyl chloride); polyacrylic acid; ethylene acrylic acid copolymer; ethylene vinyl acetate copolymer; polyvinyl alcohol; poly(hydroxyl alkylmethacrylate); Polyvinyl esters (e.g. polyvinyl acetate); and/or copolymers, blends, and/or composites of above. Non-limiting examples of polymers that can be made to be biodegradable and/or bioresorbable with modification include, but are not limited to, hyaluronic acid (hyanluron); polycarbonates; polyorthocarbonates; copolymers of vinyl monomers; polyacetals; biodegradable polyurethanes; polyacrylamide; polyisocyanates; polyamide; and/or copolymers, blends, and/or composites of above. As can be appreciated, other and/or additional polymers and/or derivatives of one or more of the above listed polymers can be used. The one or more polymers can be coated by a variety of mechanisms such as, but not limited to, spraying (e.g., atomizing spray techniques, etc.), dip coating, roll coating, sonication, brushing, plasma deposition, and/or depositing by vapor deposition. The thickness of each polymer layer is generally at least about 0.01 μm and is generally less than about 150 μm; however, other thicknesses can be used. In one non-limiting embodiment, the thickness of a polymer layer and/or layer of biological agent is about 0.02-75 μm, more particularly about 0.05-50 μm, and even more particularly about 1-30 μm. As can be appreciated, other thicknesses can be used. When the physical hindrance includes a sheath, the sheath can be designed to partially or fully encircle the medical device. The sheath can be designed to be physically removed from the medical device after the medical device is deployed to a treatment area; however, this is not required. The sheath can be formed of a biodegradable material that at least partially degrades over time to at least partially expose one or more surface regions, micro-structures and/or surface structures of the medical device; however, this is not required. The sheath can include and/or be at least partially coated with one or more biological agents. The sheath includes one or more polymers; however, this is not required. The one or more polymers can be used for a variety of reasons such as, but not limited to, 1) forming a portion of the sheath, 2) improving a physical property of the sheath (e.g., improve strength, improve durability, improve biocompatibility, reduce friction, etc.), and/or 3 at least partially controlling a release rate of one or more biological agents from the sheath. As can be appreciated, the one or more polymers can have other or additional uses on the sheath.

It is one non-limiting object of the invention to provide for a medical adhesive for use in conjunction with a medical device.

It is another and/or alternative non-limiting object of the invention to provide a medical adhesive for physically retaining a medical device in a particular form and/or on a particular deployment device until the medical device is properly positioned.

It is still another and/or alternative non-limiting object of the invention to provide for a medical adhesive that includes at least biological agent.

It is yet another and/or alternative non-limiting object of the present invention to provide a medical adhesive that includes a marker material.

These and other objects and advantages will become apparent from the following description taken together with the accompanying drawings.

BRIEF DESCRIPTION OF THE DRAWINGS

Reference may now be made to the drawings, which illustrate an embodiment that the invention may take in physical form and in certain parts and arrangements of parts wherein.

DETAILED DESCRIPTION OF THE INVENTION

Figure 1:
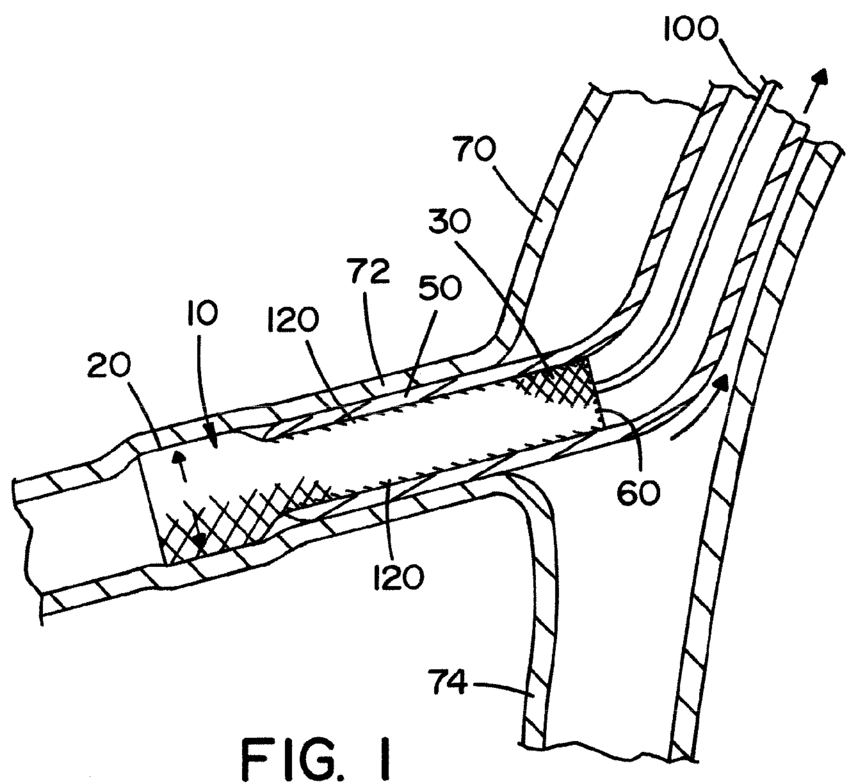
FIG. 1 illustrates a stent and a delivery device positioned at the ostium of a vessel with the sheath about to be retracted.
Figure 2:
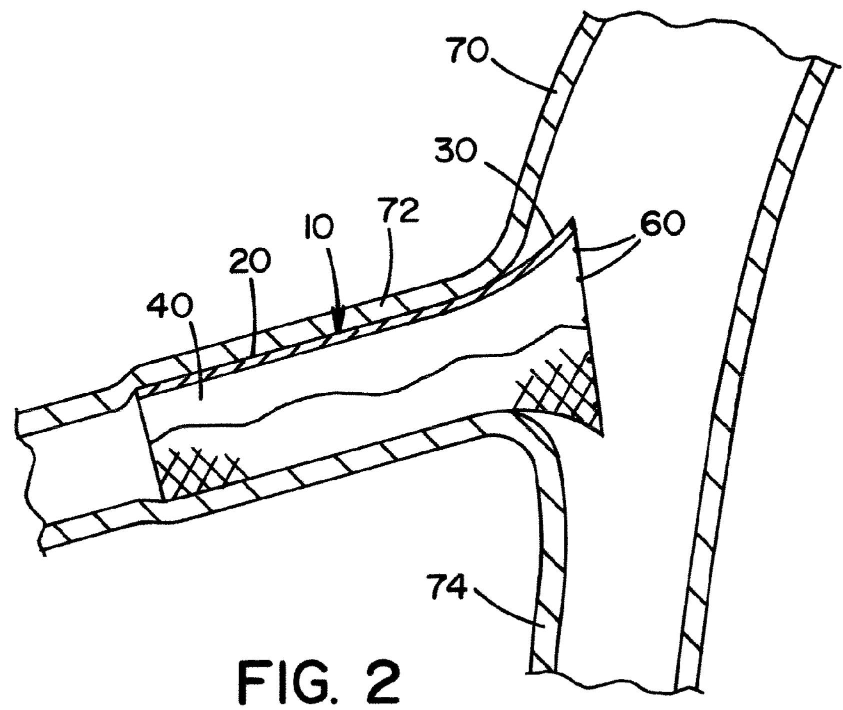
FIG. 2 illustrates a stent in the fully extended position placed within the vessel and its ostium with the flared section of the stent positioned against the wall of the originating organ.

Referring now to the drawings wherein the showings are for the purpose of illustrating the preferred embodiment only and not for the purpose of limiting the same, FIGS. 1-2 illustrate two non-limiting applications of the medical adhesive of the present invention. The figures illustrate the use of the medical adhesive in conjunction with a particular type of vascular stent 10. As can be appreciated, the medical adhesive can be used with other type of vascular stents and/or other types of medical devices.

Figure 3:
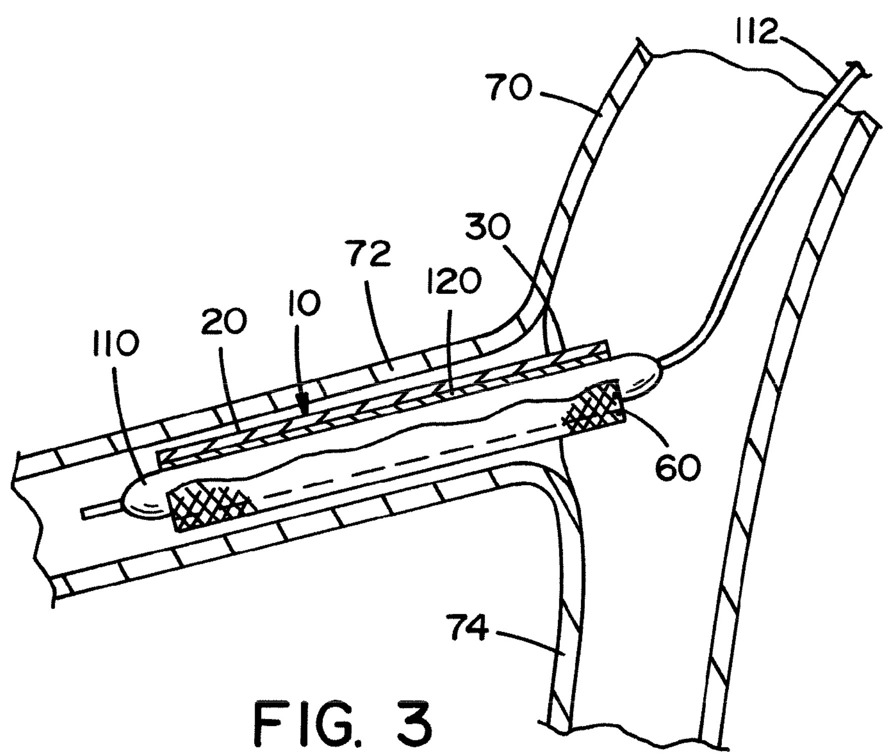
FIG. 3 illustrates a stent and an alternative delivery device positioned at the ostium of a vessel; and, FIG. 4 illustrates a stent and delivery device positioned at the ostium of a vessel with delivery device in an expanded state.
Figure 4:
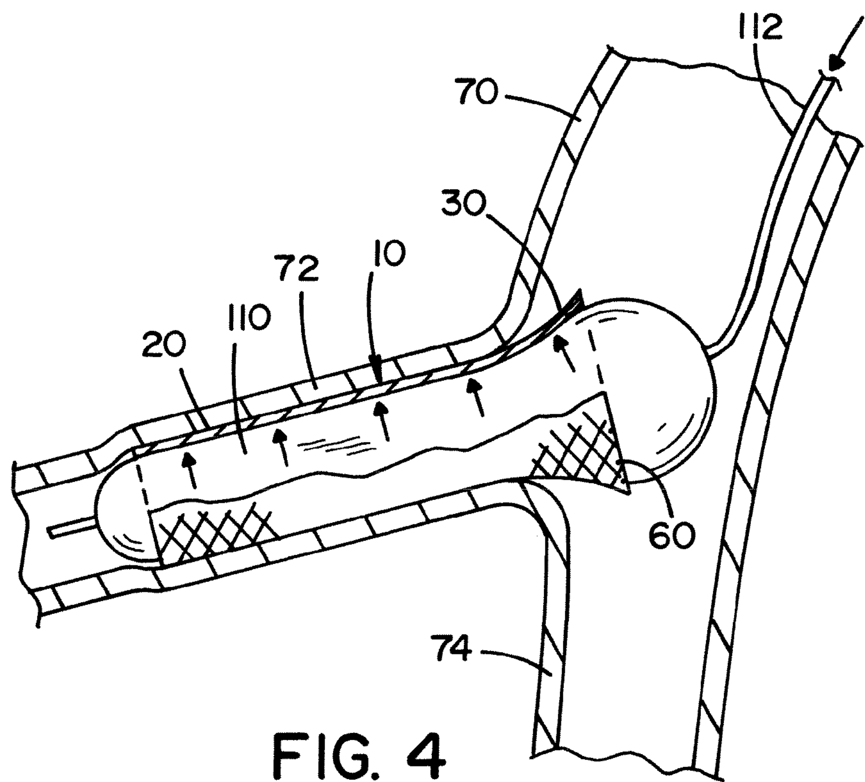

As best illustrated in FIGS. 2 and 4, the vascular stent 10 includes an expandable body section 20 and a flaring section 30. The body section 20 has a generally uniform tubular shape along the longitudinal axis of the vascular stent; however, will be appreciated that the body section can have other shapes. The body section has a generally constant diameter in the expanded state; however, this is not required. Typically, the body section has a generally uniform tubular shape in the unexpanded state; however, this is not required. The flaring section 30 is illustrated in the expanded state as a diverging tubular shape or frustoconical shape. The diameter of the flaring section increases along the longitudinal length of the vascular stent. The flare angle of the flaring section in the expanded state is illustrated as nonlinear along the longitudinal axis of the vascular stent. As such, the angle of flare of the flare section increases from 0° relative to a longitudinal axis of the vascular stent to a maximum flare angle at a nonlinear angular rate. As illustrated in FIGS. 2 and 4, the flaring section has a smaller longitudinal length than the body section. Generally, the body section constitutes at least about 60 percent of the longitudinal length of the vascular stent; however, it can be appreciated that the body section can constitute other percentages of the longitudinal length of the vascular stent. The flaring section and the body section of the vascular stent are illustrated as formed from a plurality of intersecting wires or members. It can be appreciated that the flaring section and the body section can be formed in a variety of ways, and is not limited to the plurality of intersecting wires or members as illustrated in FIGS. 1-4.

Prior to and during percutaneous insertion of the vascular stent into a tubular organ, the body section and the flaring section in the unexpanded state has a generally uniform tubular shape; however, this is not required. Once the vascular stent has been delivered to the desired location in a tubular organ, the vascular stent is expanded and/or allowed to expand to its expanded state as illustrated in FIGS. 2 and 4. The geometric configuration of the walls of the vascular stent can vary for differing specific applications depending upon the requirements for rigidity, radial strength and flexibility. A central passageway 40 exists along the longitudinal axis of the vascular stent. The diameter of the passageway when the vascular stent is in an expanded state is sufficient to allow various fluids (e.g., blood, etc.) to pass through the vascular stent when it has been set in a tubular organ.

Referring now to FIGS. 1 and 3, the vascular stent can be collapsed into its unexpanded state and be at least partially positioned in the vessel ostium by a delivery device. The vascular stent can include one or more markers such as radiopaque markers 60 at one or both ends of the vascular stent as well as the location of the demarcation between the body section and the flaring section so as to allow for better and more precise positioning of the vascular stent in a tubular organ. The vascular stent can be positioned in the vessel ostium using standard fluoroscopic and angiographic techniques. The vascular stent can be fabricated in different sizes to allow stenting of a wide variety of vessels or tubular passageways. Applications in which the vascular stent can be used, but are not limited to, the ostial of the left main coronary artery, right coronary artery, innominate artery, left common carotid artery, subclavian artery, vertebral arteries, renal arteries, hepatic artery, and mesenteric arteries. Venous applications are also possible such as, but not limited to, the aorto-ostial anastomoses of saphenous vein grafts used in coronary artery bypass grafting.

In one non-limiting technique, the delivery device includes the use of a sheath 50 that can be retracted from the vascular stent to allow the vascular stent to expand to its expanded state. As shown in FIG. 1, vascular stent 10 is in the collapsed position or unexpanded state, constrained within the confines of retractable sheath 50. FIG. 1 illustrates the vascular stent in a retractable sheath delivery system inserted within a vessel 72 at its ostium with the sheath 50 of the delivery system being partially withdrawn after placement of the vascular stent 10. In one non-limiting example, vessel 70 can represent the left main (LM) coronary artery, vessel 72 can represent the left circumflex (LCx) coronary artery, and vessel 74 can represent the left anterior descending (LAD) coronary artery. As can be appreciated, the vascular stent can be inserted into other vessels or body passageways. As shown in FIG. 1, the vascular stent 10 is guided into the LCx by the delivery device. The delivery device is illustrated as including a guide rod 100 in combination with a sheath 50; however, it will be appreciated that other delivery systems could be used. A medical adhesive 120 is shown to be positioned between the outer surface of the vascular stent and the inner surface of the sheath. The medical adhesive is used to at least partially retain the vascular stent on the sheath while the vascular stent is inserted into the blood vessel 72. The vascular stent is typically positioned so that the flaring section of the vascular stent sticks slightly out or protrudes in the LM prior to the expansion of the flaring section. Typically the full portion of the flaring section protrudes into the LM coronary artery; however, this is not required. The flaring section of the vascular stent is positioned to protrude into the LM coronary artery prior to the vascular being expanded so as to substantially fully cover the ostium of the LCx. As the sheath is removed from the vascular stent, the medical adhesive disengages from the vascular stent and/or sheath and the uncovered portion of the vascular stent expands to its expanded state to facilitate in setting the vascular stent in the vessel. As can be appreciated, an angioplasty balloon, not shown, can be used to expand or facilitate in the expansion of the body section and/or the flaring section.

Referring now to FIG. 2, sheath 50 is fully removed from the vascular stent and the vascular stent has fully expanded to its expanded state. The vascular stent is illustrated as firmly secured within vessel 72. The flaring section 30 of the vascular stent is illustrated as fully covering the ostium of vessel 72, which in this non-limiting example is the ostium of the LCx coronary artery.

The flaring section of the vascular stent covers at least a majority of the ostium and up to 100% of the ostium without protruding too far into the parent vessel as the protruding portion of the vascular stent is flared. As illustrated in FIG. 2, the flaring portion of the vascular stent also minimizes or reduces the amount of the vascular stent that extends into the parent vessel 70, which is in this non-limiting example the LM coronary artery. The flaring section 30 of the vascular stent in combination which the reduction in the amount of protrusion of the vascular stent into the parent vessel results in enough space to allow access to vessel 74, which is in this non-limiting example is the LAD coronary artery.

The expanded vascular stent can include some medical adhesive after the sheath is removed. Typically the medical adhesive is a biocompatible material. The medical adhesive is typically a biodegradable material; however, this is not required. The medical adhesive can include one or more biological agents that can be used to provide localized dosages of such biological agents to the treated area. The one or more biological agents can be used to facilitate in the healing of the treated area, reduce pain in the treated area, reduce rejection of the vascular stent in the treated area, reduce restenosis and/or subacute thrombosis, reduce infection; and/or the like. The one or more biological agents in the medical adhesive can be controllably and/or uncontrollably released from the medical adhesive.

Referring now to FIGS. 3 and 4, the expansion of the vascular stent can at least partially result from the inflation of a balloon and/or by use of shape memory materials to form the vascular stent. When a balloon 110 is used as illustrated in FIG. 4, the balloon is at least partially positioned in the unexpanded vascular stent. Once the vascular stent is properly positioned in a vessel, the balloon is expanded by a tube 112 to cause the vascular stent to at least partially expand to its expanded state. The balloon can be inflated prior to, during and/or after the sheath 50 has been at least partially removed from the vascular stent. After the balloon has at least partially expanded the vascular stent, the balloon is typically at least partially deflated and removed from the passageway of the vascular stent. As can be appreciated, the sheath and balloon delivery systems can be separate delivery systems that are used mutually exclusive on one another. As such the delivery system may only involve the use of a balloon or the use of a sheath.

As shown in FIGS. 3 and 4, a medical adhesive is used to at least partially secure the vascular stent 10 to balloon 110 during the insertion of the vascular stent into a vessel. In this embodiment, the delivery device includes a balloon 110 that is at least partially connected to the interior surface of the vascular stent 10 by medical adhesive 120. As can be appreciated, the delivery device can also include a sheath that can be retracted from the vascular stent to allow the vascular stent to expand to its expanded state as illustrated in FIGS. 1 and 2. As shown in FIG. 3, vascular stent 10 is in the collapsed position or unexpanded state, constrained by the at least partially deflated balloon and medical adhesive 120. The collapsed vascular stent 10 is inserted into a vascular system by the delivery system and placed within vessel 72 at its ostia. In one non-limiting example, vessel 70 can represent the LM, vessel 72 can represent the LCx, and vessel 74 can represent the LAD. As can be appreciated, the vascular stent can be inserted into other vessels or body passageways. As shown in FIG. 4, the vascular stent 10 is guided into the LCx by the delivery device. Typically, the flaring section of the vascular stent sticks slightly out in the LM prior to the expansion of the flaring section. As balloon 110 is inflated, the vascular stent expands to its expanded state to facilitate in setting the vascular stent in the vessel. The expansion of the balloon causes the medical adhesive between the balloon and the vascular stent to break down or otherwise release from the balloon and/or vascular stent; thereby at least partially releasing the vascular stent from the balloon. Once the vascular stent has been expanded, the balloon is at least partially deflated. Due to the break down or otherwise release from the balloon and/or vascular stent of the medical adhesive during the expansion of the vascular stent, the balloon can be removed from the vascular stent when the balloon is at least partially deflated without causing the vascular stent to be dislodged or be repositioned by the removal of the balloon from the vascular stent. As can be appreciated, some medical adhesive may be left on the balloon and/or vascular stent after the removal of the balloon. Typically the medical adhesive is a biocompatible material. The medical adhesive is typically a biodegradable material; however, this is not required. The medical adhesive can include one or more biological agents that can be used to provide localized dosages of such biological agents to the treated area. The one or more biological agents can be used to facilitate in the healing of the treated area, reduce pain in the treated area, reduce rejection of the vascular stent in the treated area, reduce restenosis and/or subacute thrombosis, reduce infection; and/or the like. The one or more biological agents in the medical adhesive can be controllably and/or uncontrollably released from the medical adhesive. The medical adhesive can be sprayed, painted, dipped, etc on the vascular stent. One or more surfaces of the vascular stent can include the medical adhesive. The medical adhesive can be formulated to withstand sterilization of the vascular stent; however, this is not required.

It will thus be seen that the objects set forth above, among those made apparent from the preceding description, are efficiently attained, and since certain changes may be made in the constructions set forth without departing from the spirit and scope of the invention, it is intended that all matter contained in the above description and shown in the accompanying drawings shall be interpreted as illustrative and not in a limiting sense. The invention has been described with reference to preferred and alternate embodiments. Modifications and alterations will become apparent to those skilled in the art upon reading and understanding the detailed discussion of the invention provided herein. This invention is intended to include all such modifications and alterations insofar as they come within the scope of the present invention. It is also to be understood that the following claims are intended to cover all of the generic and specific features of the invention herein described and all statements of the scope of the invention, which, as a matter of language, might be said to fall therebetween.

We claim:

1. A method for applying a medical device to a treatment area comprising:

a) selecting an expandable medical device, said medical device including a medical adhesive, a stent conveying device, an expandable stent releasably secured to said stent conveying device, and a sheath positioned at least at least partially about said stent, said stent including a body portion expandable from a first cross-sectional area to an expanded and larger second cross-sectional area, said body portion of said expandable stent including a first body portion and a flaring section, said first body portion having a body diameter, said flaring section having a flaring diameter, said body diameter and said flaring diameter being different when said first body portion and said flaring section are in an expanded state, said flaring diameter on at least a portion of said flaring section being greater than said body diameter of said first body portion in an expanded state, said stent conveying device designed to convey said stent in said first cross-sectional area to the treatment area in a body passageway, said stent conveying device including a catheter, a balloon, or combinations thereof, said medical adhesive formulated to a) at least partially retain said expandable stent on said stent conveying device until said expandable stent is conveyed to the treatment site and deployed at said treatment site, b) at least partially maintain said body of said expandable stent in said first cross-sectional area until said expandable stent is conveyed to the treatment site and deployed at said treatment site, c) at least partially retain said sheath on said expandable stent until said expandable stent is conveyed to the treatment site and deployed at said treatment site, or and combination of a), b) or c);

b) deploying said expandable stent to said treatment area by said stent conveying device while said expandable stent on said stent conveying device is in said first cross-sectional area;

c) at least partially removing said sheath from said first body portion of said expandable stent to enable at least a portion of said first body portion of said expandable stent to expand from said first cross-sectional area to said second cross-sectional area while said flaring portion is retained by said sheath in said first cross-section area, said expansion of said first body portion prior to expansion of said flaring portion causing said stent to be set in position in the body passageway prior to said flaring portion being expanded to said second cross-section area;

d) removing said sheath from said flaring portion and expanding said flaring portion of said expandable stent at said treatment area; and, e) removing said stent conveying device from said treatment area while said expandable stent remains at said treatment area, wherein said step of removing said sheath, step of expanding said stent, or combinations thereof causing said medical adhesive to a) release said expandable stent from said stent conveying device and to allow said body of said expandable stent to expand to said second cross-sectional area, b) release said sheath from said expandable stent so that said sheath can at least partially removed from said expandable stent, or a) and b).

2. The method as defined in claim 1, wherein said expandable stent includes a plurality of microstructures, said plurality of said micro-structures extend upwardly from and above at least a portion of said expandable stent, said plurality of microstructures having a shape and size to penetrate into said body passageway at said treatment site when said body of said expandable stent is expanded to said second cross-sectional area, said plurality of microstructures having a height of less than 400 microns, said plurality of microstructures a) at least partially maintaining said stent at said treatment area when said plurality of microstructures penetrate into said body passageway, b) delivering a biological agent in said penetrated region of said body passageway at said treatment area, or combinations thereof.

3. The method as defined in claim 1, wherein said medical adhesive includes at least one biological agent, said at least one biological agent includes an agent selected from the group consisting of trapidil, trapidil derivatives, taxol, taxol derivatives, cytochalasin, cytochalasin derivatives, paclitaxel, paclitaxel derivatives, rapamycin, rapamycin derivatives, reversitrol, reversitrol derivatives, GM-CSF, GM-CSF derivatives, or combinations thereof.

4. The method as defined in claim 2, wherein said medical adhesive, said plurality of microstructures, or combinations thereof include at least one biological agent, said at least one biological agent includes an agent selected from the group consisting of trapidil, trapidil derivatives, taxol, taxol derivatives, cytochalasin, cytochalasin derivatives, paclitaxel, paclitaxel derivatives, rapamycin, rapamycin derivatives, reversitrol, reversitrol derivatives, GM-CSF, GM-CSF derivatives, or combinations thereof, said plurality of microstructures at least partially coated with biological agent, at least partially made of biological agent, include biological agent in an internal passage of said microstructure, at least partially formed of said medial adhesive, or combinations thereof.

5. The method as defined in claim 4, wherein said medical adhesive, said plurality of microstructures, or combinations thereof includes a polymer that enables controlled release of at least biological agent from said medical adhesive, said plurality of microstructures, or combinations thereof.

* * * * *